United States Patent
Kumazawa et al.

(10) Patent No.: US 10,251,765 B2
(45) Date of Patent: Apr. 9, 2019

(54) STENT DELIVERY SYSTEM AND MANUFACTURING METHOD FOR THE SAME

(71) Applicant: Terumo Kabushiki Kaisha, Shibuya-ku (JP)

(72) Inventors: Takashi Kumazawa, Kanagawa (JP); Hiroaki Nagura, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 554 days.

(21) Appl. No.: 13/627,538

(22) Filed: Sep. 26, 2012

(65) Prior Publication Data
US 2013/0023977 A1 Jan. 24, 2013

Related U.S. Application Data
(63) Continuation of application No. PCT/JP2011/052031, filed on Feb. 1, 2011.

(30) Foreign Application Priority Data

Mar. 30, 2010 (JP) ................................. 2010-076502

(51) Int. Cl.
*A61F 2/958* (2013.01)
*A61F 2/915* (2013.01)

(52) U.S. Cl.
CPC .............. *A61F 2/958* (2013.01); *A61F 2/915* (2013.01); *A61F 2002/91558* (2013.01);
(Continued)

(58) Field of Classification Search
CPC .............. A61F 2/958; A61F 2002/9583; A61F 2002/9586; A61F 2002/9522; A61F 2/95;
(Continued)

(56) References Cited

U.S. PATENT DOCUMENTS 5,836,965 A 11/1998 Jendersee et al.
5,954,740 A * 9/1999 Ravenscroft et al. ........ 606/194
(Continued)

FOREIGN PATENT DOCUMENTS

JP 2002-539888 A 11/2002
JP 2009-540928 A 11/2009

OTHER PUBLICATIONS

International Search Report (PCT/ISA/210) dated Mar. 8, 2011, by the Japan Patent Office as the International Searching Authority for International Application No. PCT/JP2011/052031.
(Continued)

*Primary Examiner* — Diane D Yabut
*Assistant Examiner* — Majid Jamialahmadi
(74) *Attorney, Agent, or Firm* — Buchanan Ingersoll & Rooney PC (57) ABSTRACT

A stent delivery system, and associated manufacturing method, are such that the outer diameter of the distal portion of the stent delivery system is relatively small. The stent delivery system includes a hollow shaft portion, an inflatable balloon disposed on the outer periphery of a distal portion of the shaft portion, and a stent disposed on the outer periphery of the balloon and having struts expanded by inflation of the balloon. The balloon has a ridge portion with which the stent is engaged. The ridge portion is sandwiched in a space between the struts, and a top portion of the ridge portion has a concave portion recessed toward the axis of the shaft portion.

16 Claims, 10 Drawing Sheets

(52) U.S. Cl.
CPC .............. *A61F 2002/9583* (2013.01); *A61F 2230/0013* (2013.01); *A61F 2230/0054* (2013.01); *Y10T 29/49826* (2015.01)

(58) Field of Classification Search
CPC ... A61M 2025/1086; B29C 2049/4879; B29C 2049/4882; B23P 11/00; B23P 11/005; Y10T 29/49863; Y10T 29/49913; Y10T 29/49915; Y10T 29/49911
USPC ..... 623/1.11, 1.12, 1.2, 1.15, 1.23; 606/191, 606/192, 108, 198, 194; 29/508, 282, 29/428, 454, 515; 264/523, 313
See application file for complete search history.

(56) References Cited

U.S. PATENT DOCUMENTS

| | | | |
|---|---|---|---|
| 6,258,099 B1 * | 7/2001 | Mareiro et al. | 606/108 |
| 6,315,708 B1 * | 11/2001 | Salmon | A61F 2/90 600/3 |
| 6,464,718 B1 * | 10/2002 | Miller et al. | 623/1.11 |
| 7,572,270 B2 * | 8/2009 | Johnson | 606/194 |
| 8,046,897 B2 * | 11/2011 | Wang et al. | 29/515 |
| 8,221,484 B2 * | 7/2012 | Wesselmann | 623/1.11 |
| 2002/0120321 A1 * | 8/2002 | Gunderson et al. | 623/1.11 |
| 2007/0289117 A1 | 12/2007 | Huang et al. | |

OTHER PUBLICATIONS

Official Action issued by Japanese Patent Office dated May 26, 2015 in Japanese Application No. 2012-508122, and English language translation of Official Action (6 pgs).

Decision of Rejection issued by Japanese Patent Office dated Dec. 1, 2015 in Japanese Application No. 2012-508122, and English language translation thereof (6 pgs).

* cited by examiner

Initial State

FIG. 6

Expansion State

STENT DELIVERY SYSTEM AND MANUFACTURING METHOD FOR THE SAME

CROSS REFERENCES TO RELATED APPLICATIONS

This application is a continuation of International Application No. PCT/JP2011/052031 filed on Feb. 1, 2011, and claims priority to Japanese Patent Application JP2010-076502 filed in the Japanese Patent Office on Mar. 30, 2010, the entire content of both of which is incorporated herein by reference.

TECHNICAL FIELD

The present invention generally relates to a stent delivery system and a method for manufacturing a stent delivery system.

BACKGROUND DISCUSSION

A stent delivery system is a system by which a stent used for improving a stenosis or an occlusion region in a lumen in a living body is inserted into and indwelled at a target region (stenosis or occlusion region). The stent delivery system includes an inflatable balloon disposed on an outer periphery of a distal portion of a hollow shaft portion and a stent disposed on an outer periphery of the balloon and having struts expanded by inflation of the balloon.

Since the balloon includes ridge portions through which the stent is engaged therewith, in a process in which a distal portion of the stent delivery system is inserted into a lumen and is positioned at a target region and then the balloon is inflated to plastically deform the stent so that the stent is closely contacted with and indwelled on an inner surface of the target region, positional displacement and detachment (separation) of the stent from the balloon are suppressed.

The ridge portions of the balloon are formed by inflating, when the stent delivery system is manufactured, the balloon so that part of the balloon projects into spaces between struts and the projected portions are sandwiched by the struts. An example of this is disclosed in U.S. Pat. No. 5,836,965.

However, the ridge portions of the balloon in the conventional technique project from the spaces between the struts to the outside, which increases an outer diameter of the distal portion of the stent delivery system. Therefore, there is a problem that a lumen to which the stent delivery system can be applied is limited.

SUMMARY

An aspect of the disclosure here involves a stent delivery system having a hollow shaft portion, an inflatable balloon disposed on the outer periphery of the hollow shaft at a distal portion of the shaft portion, and an expandable stent disposed on the outer periphery of the balloon and expandable by inflation of the balloon. The balloon possesses a ridge portion with which the stent is engaged, and the ridge portion is sandwiched in a space between the struts. In addition, the top portion of the ridge portion has a concave portion recessed toward the axis of the shaft portion Another aspect involves a stent delivery system comprising: a hollow shaft; an inflatable balloon fixed to the outer periphery of the hollow shaft in a liquid-tight manner, with a lumen communicating with the interior of the balloon to introduce inflation fluid into the balloon interior to inflate the balloon, the balloon possessing an outer periphery; an expandable stent comprised of a plurality of interconnected struts, with the interconnected struts being arranged to define a plurality of spaced apart spaces each bounded by several of the struts; and the expandable stent being mounted on the balloon in surrounding relation to the balloon, with the struts contacting the outer periphery of the balloon, so that inflation of the balloon expands the stent. The balloon possesses a plurality of spaced ridge portions each projecting outwardly relative to immediately surrounding portions of the balloon, with each of the ridge portions being located in a respective one of the spaces of the stent so that the ridge portions are sandwiched in the respective spaces. A center part of a plurality of the ridge portions is recessed radially inwardly toward the axis of the shaft portion so that each recessed center part is bounded by parts of the ridge portion that are upstanding relative to the central part.

A further aspect of the disclosure here involves a method for manufacturing a stent delivery system which has a hollow shaft portion, an inflatable balloon disposed on the outer periphery of the distal end portion of the shaft portion, and an expandable stent disposed on the outer periphery of the balloon and having struts surrounding respective spaces. The manufacturing method involves inflating the balloon so that part of the balloon projects into a space between the struts such that the projecting portion is sandwiched by the struts to form a ridge portion through which the stent is engaged with the balloon, and forming a concave portion recessed toward the axis of the shaft portion at a top portion of the ridge portion.

With the stent delivery system disclosed here, since the top portion of the ridge portion of the balloon with which the stent is engaged has the concave portion recessed toward the axis of the shaft portion, positional displacement and detachment (separation) of the stent from the balloon are avoided and an increase in the outer diameter of the distal portion is suppressed. Accordingly, the stent delivery system in which the outer diameter of the distal portion is relatively small can be provided.

Where the ridge portion of the balloon is positioned the inside of the space between the struts and does not project to the outside, an increase of the outer diameter of the distal portion is suppressed still more. Therefore, the outer diameter of the distal portion can be minimized.

The manufacturing method forms the concave portion, which is recessed toward the axis of the shaft portion, on the top portion of the ridge portion of the balloon with which the stent is engaged, and so the likelihood of positional displacement and detachment (separation) of the stent from the balloon is reduced, and an increase in the outer diameter of the distal portion in the stent delivery system to be manufactured can be avoided. Accordingly, the manufacturing method for the stent delivery system in which the outer diameter of the distal portion is relatively small can be provided.

Where the balloon is inflated by applying pressure to the balloon to form the ridge portion on the balloon and then the pressure applied to the balloon is reduced, the concave portion can be fairly easily formed at the top portion of the ridge portion. By reducing the diameter of the stent and the balloon themselves, decrease of the outer diameter of the distal portion is achieved and engagement strength between the stent and the balloon can be increased.

With the concave portion formed at the top portion of the ridge portion of the balloon to position the ridge portion in the inside of the space between the struts, the ridge portion does not project to the outside and increase of the outer diameter of the distal portion is suppressed still more. Therefore, the outer diameter of the distal portion can be minimized.

Other aspects, features and characteristics of the stent delivery system and manufacturing method will become more apparent from the following detailed description considered with reference to the accompanying drawing figures which are briefly discussed below.

DETAILED DESCRIPTION

Figure 1:
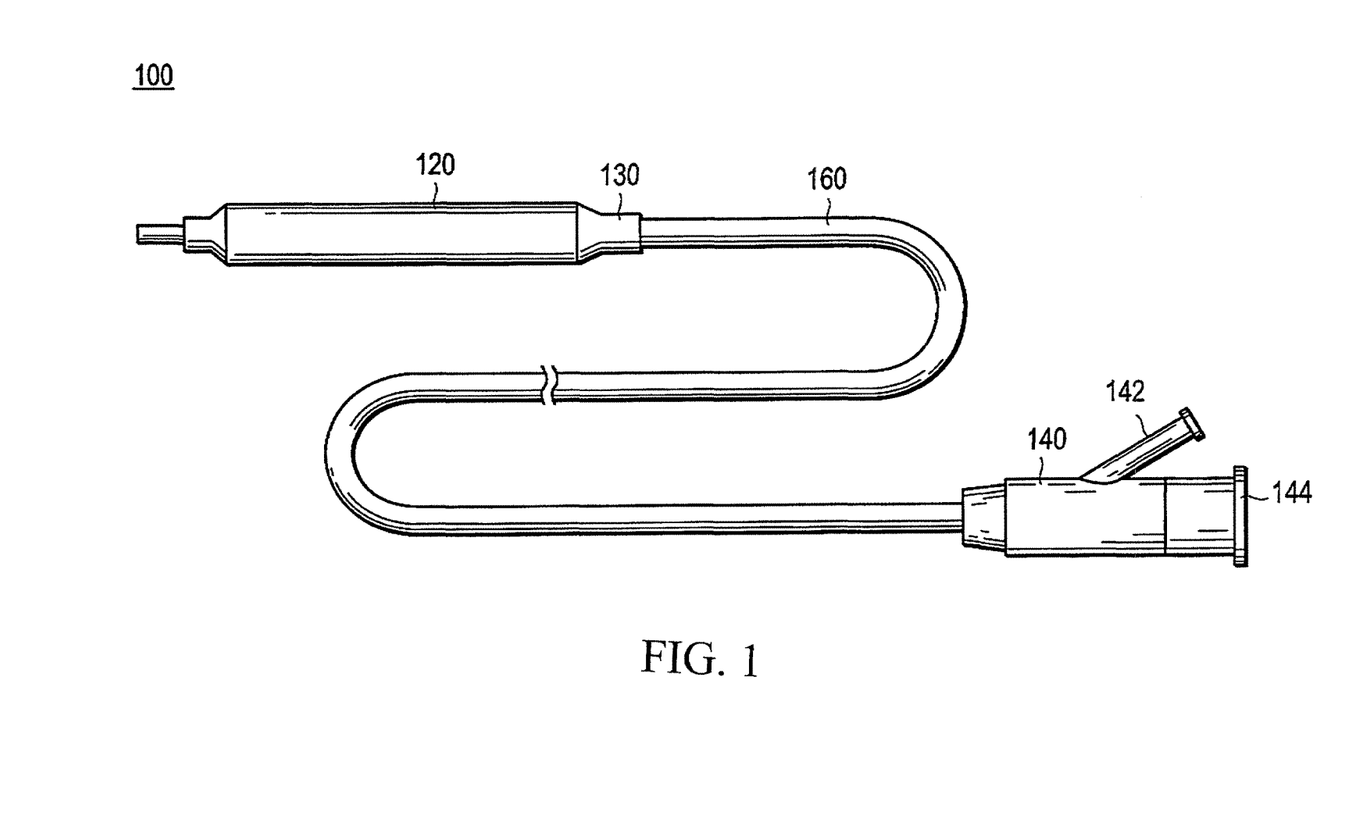
FIG. 1 is a schematic view illustrating a stent delivery system according to an embodiment representing one example of the stent delivery system disclosed here.
Figure 2:
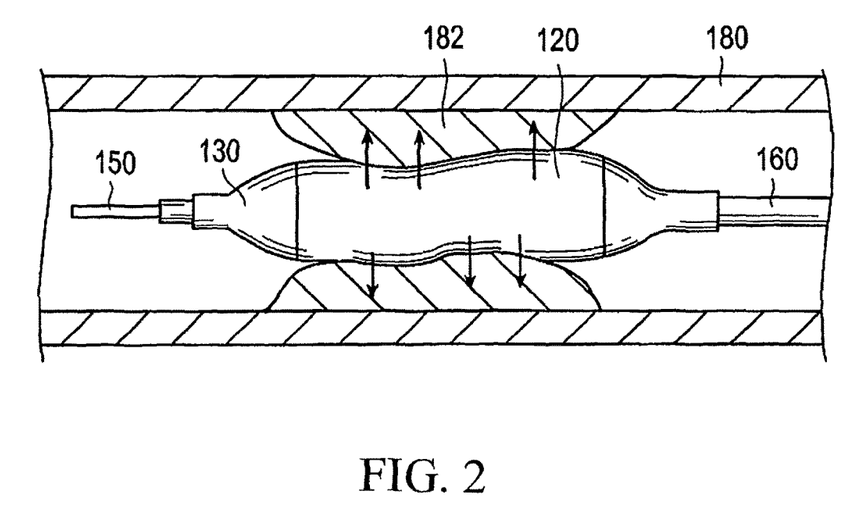
FIG. 2 is a schematic view illustrating a use of the stent delivery system shown in FIG. 1.

Referring initially to FIGS. 1 and 2, an embodiment of the stent delivery system (or in other words, living organ dilator) 100 representing one example of the stent delivery system disclosed here is generally described. The stent delivery system is used to insert and indwell a stent, which has a distal portion having a relatively small outer diameter and is used for improving a stenosis (or an occlusion region) 182 appearing in a lumen 180 in a living body, into and at the stenosis 182. The stent delivery system 100 includes a hollow shaft portion 160, a balloon 130 disposed on an outer periphery at a distal portion of the shaft portion 160, a stent 120 disposed on an outer periphery of the balloon 130 and a hub 140 positioned at a proximal portion of the shaft portion 160.

For example, the lumen 180 in the living body is a coronary artery of a heart, and one of objects in improving the stenosis 182 is preventing restenosis after percutaneous transluminal coronary angioplasty (PTCA). The stent delivery system 100 can be applied not only to a stenosis appearing in a coronary artery of a heart but also to a stenosis appearing in another blood vessel, a bile duct, a trachea, an esophagus, an urethra or the like.

The stent 120 is an expandable medical device for retaining the lumen 180 in an open configuration by being closely contacted with and indwelled on an inner surface of the stenosis 182 and is configured for expansion. The stent 120 surrounds the balloon 130, and is engaged with (in contact with) the outer periphery of the balloon 130. Positional displacement and detachment (separation) of the stent 120 from the balloon 130 are suppressed. The balloon 130 is configured for inflation and is capable of expanding the stent 120 disposed on its outer periphery to increase the diameter of the stent 120.

The hub 140 has an injection port 142 and a guide wire port 144. The injection port 142 is, for example, used to introduce and discharge pressure fluid (for example, liquid such as physiological saline or angiography contrast agent) for inflating the balloon 130. The guide wire port 144 is used to insert a guide wire 150 so as the guide wire 150 projects from a distal end portion through a lumen 161 which is described below.

Indwelling of the stent 120 can be carried out in the following manner. For example, the distal portion of the stent delivery system 100 is inserted into the lumen 180 of a patient and the balloon 130 is positioned at the stenosis 182 which is a target region while the guide wire 150 projecting from the distal end portion extends distally beyond the target site. Then, pressure fluid is introduced from the injection port 142 to inflate the balloon 130 so as to cause expansion and plastic deformation of the stent 120. Then, after the stent 120 is closely contacted with the stenosis 182, the pressure of the balloon 130 is decreased to release the engagement between the stent 120 and the balloon 130 so that the stent 120 is separated from the balloon 130. The stent delivery system 100 from which the stent 120 has been separated is retracted and removed from the lumen 180.

A material forming the hub 140 is, for example, thermoplastic resin such as polycarbonate, polyamide, polysulfone, polyarylate, or methacrylate-butylene-styrene copolymer.

The distal portion of the stent delivery system 100 is now described in detail below with reference to FIGS. 3-7.

Figure 6:
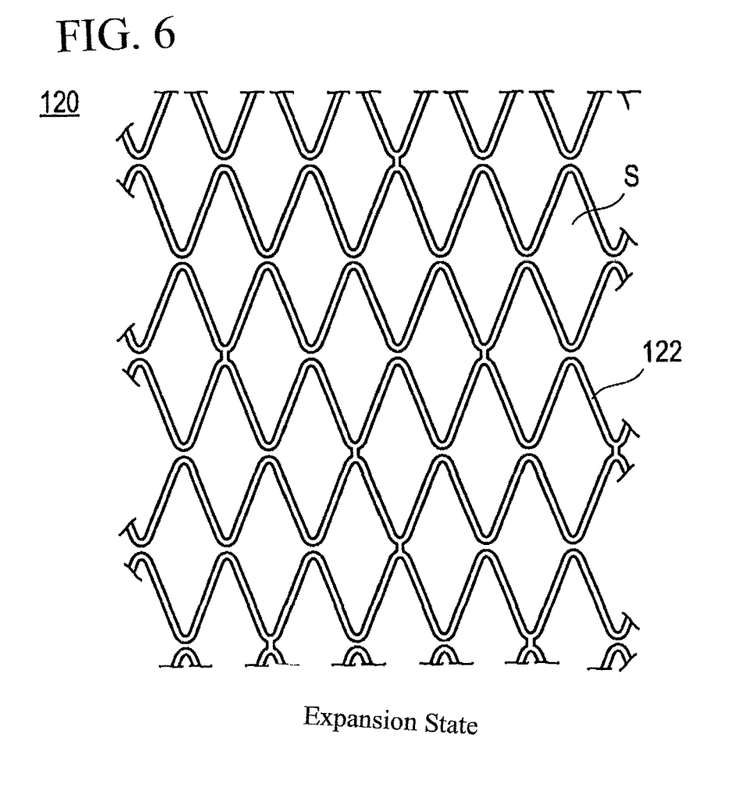
FIG. 6 is a plan view illustrating an expansion state of a stent shown in FIG. 4.

The stent 120 is formed by axially juxtaposing annular (ring) bodies each configured from a wire-like strut 122 (refer to FIG. 5) in an axial direction and connecting the annular bodies to each other. Each of the annular bodies is formed by forming straight or curved line portions and bended portions such as U-shaped portions of the struts 122 successively in wave forms on a common plane and configuring the wave-formed struts 122 in an annular shape. The annular body is expandable as shown in FIG. 6 such that the diameter can be decreased when the stent is inserted from the outside of the body into the inside of the body.

The stent is configured from a material having biocompatibility and formed, for example, from nickel-titanium alloy, cobalt-chromium alloy, stainless steel, iron, titanium, aluminum, tin, zinc-tungsten alloy. The stent 120 is not limited to the one shown in FIG. 5 as a wide variety of other configurations with axially positioned annular bodies connected to one another is possible.

The balloon 130 is disposed in a folded state (or in a deflated state) on the outer periphery of the distal portion of the shaft portion 160 and is inflatable. Since the stent 120 is disposed on the outer periphery of the balloon 130, the struts 122 of the stent 120 are expanded by inflation of the balloon 130.

Figure 4:
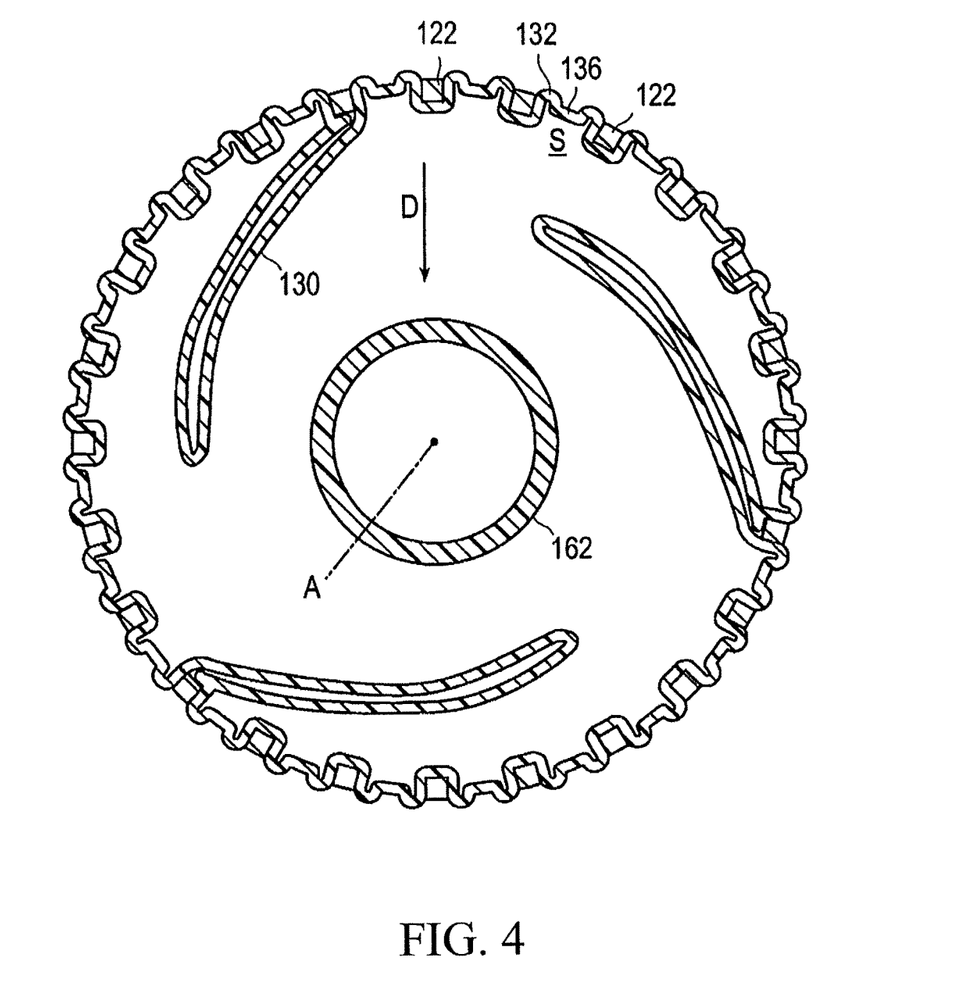
FIG. 4 is a cross-sectional view taken along the section line IV-IV of FIG. 3.
Figure 5:
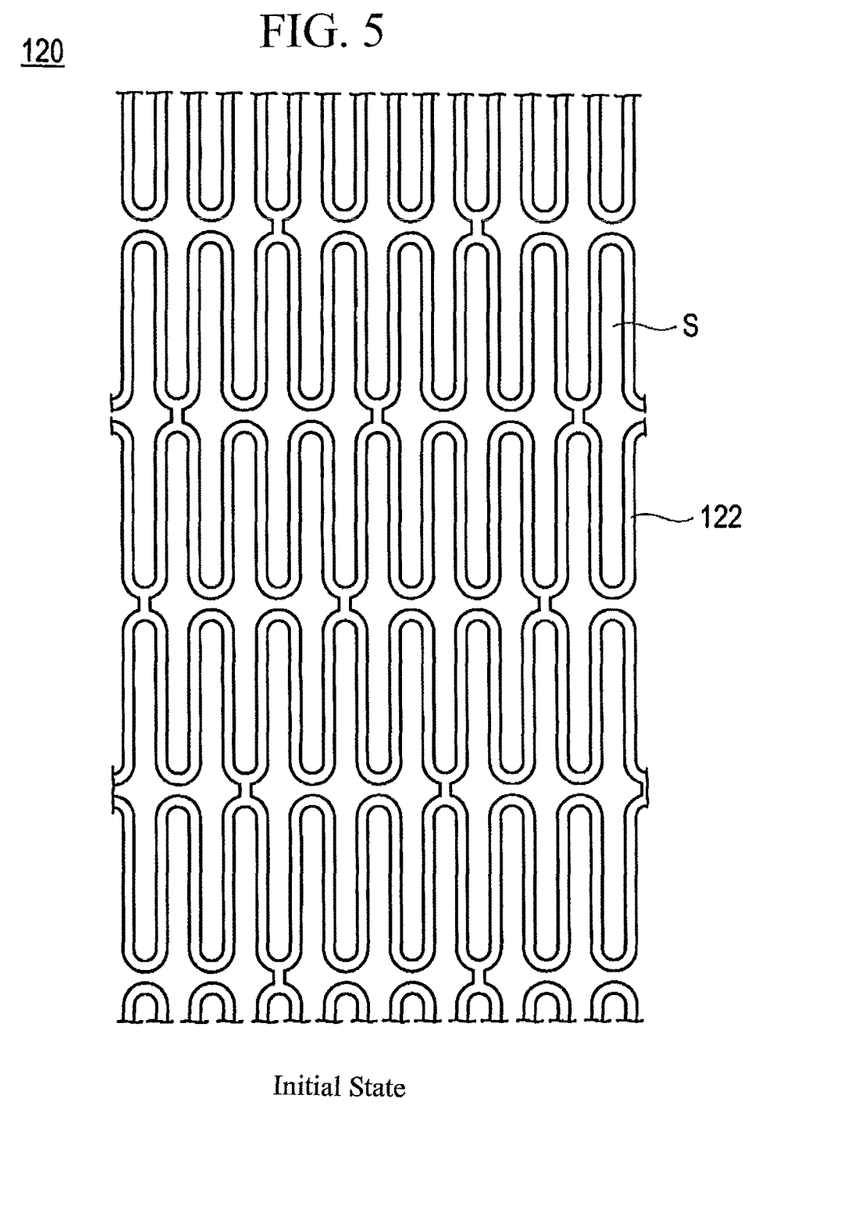
FIG. 5 is a plan view illustrating an initial state of a stent shown in FIG. 4.
Figure 7:
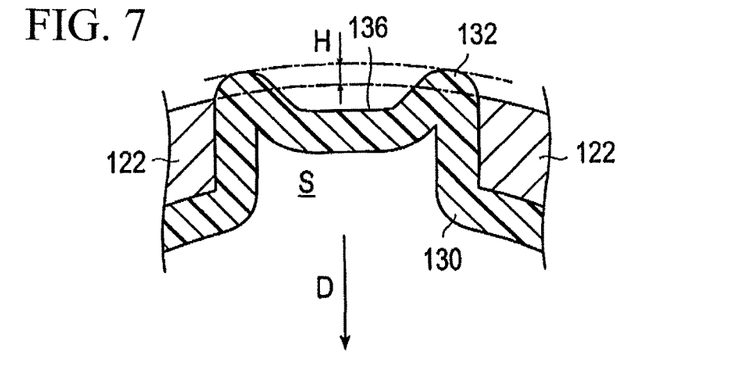
FIG. 7 is an enlarged view illustrating a ridge portion of a balloon shown in FIG. 4.

The balloon 130 has ridge portions 132 with which the stent 120 is engaged. Each of the ridge portions 132 is sandwiched in a space S, shown in FIG. 6, formed between or bounded by several of the struts 122. Each of the ridge portions 132 is thus located in one of the spaces S of the stent so that the stent 120 engages the ridge portions. The ridge portions 132 project outwardly relative to immediately surrounding portions of the balloon 130. The top of the ridge portion 132 has a concave portion 136 recessed toward an axis A of the shaft portion. In the illustrated embodiment, the concave portion 136 of each ridge portion 132 is defined by a center part of each of the ridge portions 132 being recessed radially inwardly toward the axis of the shaft portion so that each center part is a concave portion bounded by parts of the ridge portion 132 that are upstanding relative to the central part. Since a projection amount H of the ridge portion 132 by which the ridge portion 132 projects outwardly beyond the outer surface of the stent 120 decreases or is reduced due to the presence of the concave portion 136 as illustrated in FIG. 7, an increase in the outer diameter of the stent delivery system is suppressed. In particular, the outer diameter of the distal portion of the stent delivery system 100 can be decreased. Further, since a side portion of each strut 122 of the stent 120 engages ridge portions 132 on the opposite sides of the concave portion 136 of the balloon 130, positional displacement and detachment (separation) of the stent 120 from the balloon 130 are suppressed. The direction toward the axis A of the shaft portion is hereinafter referred to as the inward direction D.

As a formation material of the balloon 130, a material having flexibility is preferable. Examples include polyolefin, polyvinyl chloride, polyamide, polyamide elastomer, polyurethane, polyester such as polyethylene terephthalate, polyarylene sulfide such as polyphenylene sulfide, silicone rubber and latex rubber. Polyolefin is, for example, polyethylene, polypropylene, ethylene-propylene copolymer, ethylene-vinyl acetate copolymer, or cross-linking ethylene-vinyl acetate copolymer.

Figure 3:
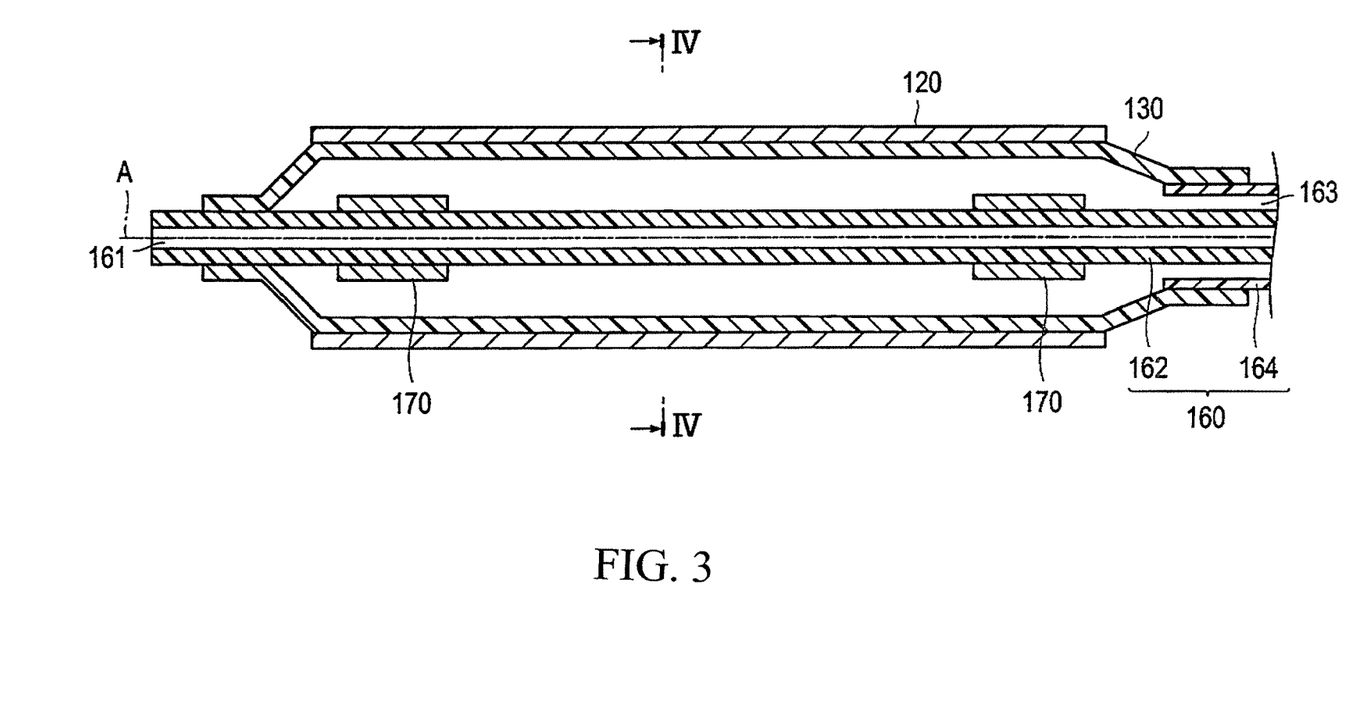
FIG. 3 is a longitudinal cross-sectional view of a distal portion of the stent delivery system shown in FIG. 1.

Generally speaking, the balloon is secured to the shaft portion 160 in a fluid-tight manner. More specifically, the shaft portion 160 is comprised of an inner tube 162 and an outer tube 164, with inner tube 162 being inserted or positioned in the outer tube 164. The inner tube 162 communicates with the guide wire port 144 of the hub 140, and extends through the balloon 130 to the distal end. Accordingly, the guide wire inserted in the guide wire port 144 passes through the inner tube 162 and is able to project from the distal end of the stent delivery system 100. The inside of the inner tube 162 constitutes a lumen 161 for guide wire insertion and guiding.

A marker 170 in the form of a tubular member is attached to the inner tube, specifically the outer surface of the inner tube 162. The marker 170 is made from a radiopaque material. Accordingly, a clear contrast image under X-ray radioscopy can be obtained and the position of the distal portion of the stent delivery system 100 can be relatively easily confirmed. The radiopaque material is, for example, platinum, gold, tungsten, iridium or alloy configured from such materials.

The outer tube 164 is disposed on an outer side of the inner tube 162 so that a space exists between the inner peripheral surface of the outer tube 164 and the outer peripheral surface of the inner tube 162. This space constitutes a lumen 163 that communicates with the injection port 142 of the hub 140. The balloon 130 is fixed in a liquid-tight manner to the outer periphery of the distal end portion of the outer tube 164 and is fixed in a liquid-tight manner to the outer periphery of the distal end portion of the inner tube 164, and the inside of the balloon 130 communicates with the lumen 163. Accordingly, pressure fluid introduced from the injection port 142 passes through the lumen 163 and is introduced into the inside of the balloon 130 so that the balloon 130 is inflated. The fixing method of the outer periphery of the distal end portion of the outer tube 164 and the balloon 130 is not specifically limited, and examples include adhesive or heat bonding.

As a forming material of the outer tube 164, a material having flexibility is preferable. Examples of materials for fabricating the outer tube 164 include polyolefin such as polyethylene, polypropylene, polybutene, ethylene-propylene copolymer, ethylene-vinyl acetate copolymer, ionomer, or mixture of two or more kinds of these materials, thermoplastic resin such as soft polyvinyl chloride resin, polyamide, polyamide elastomer, polyester, polyester elastomer, polyurethane, or fluorocarbon resin, silicon rubber and latex rubber.

As the forming material of the inner tube 162, materials similar to those of the outer tube 164 or metal materials can be utilized. Examples of the metal material include stainless steel, stainless extensible alloy or Ni—Ti alloy.

Figure 8:
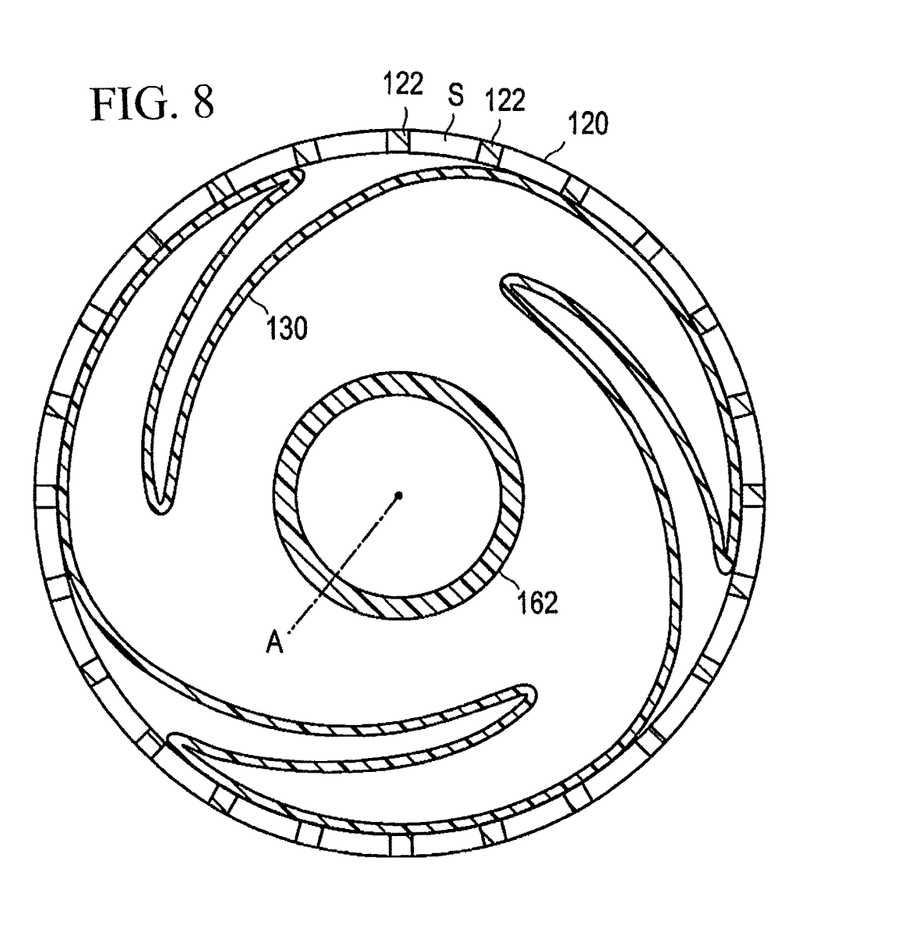
FIG. 8 is a cross-sectional view illustrating a manufacturing method for the stent delivery system shown in FIG. 1 and illustrating an initial state of the balloon and the stent.
Figure 9:
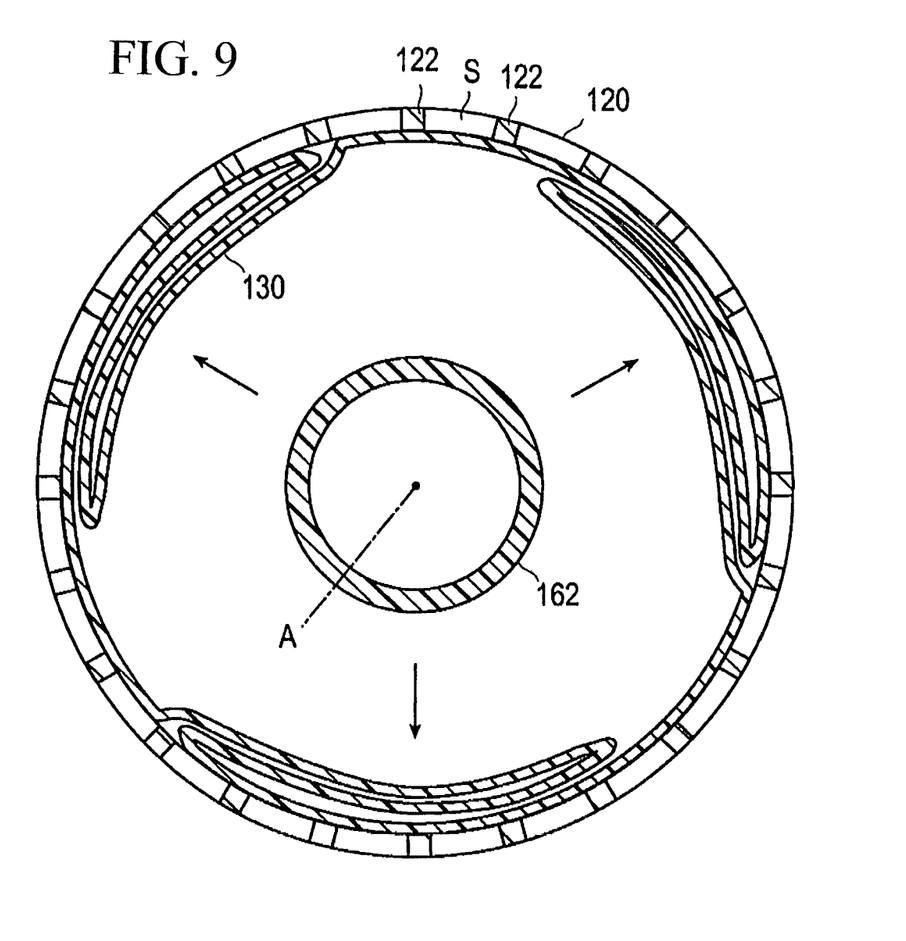
FIG. 9 is a cross-sectional view showing inflation of the balloon continuing from FIG. 8.
Figure 10:
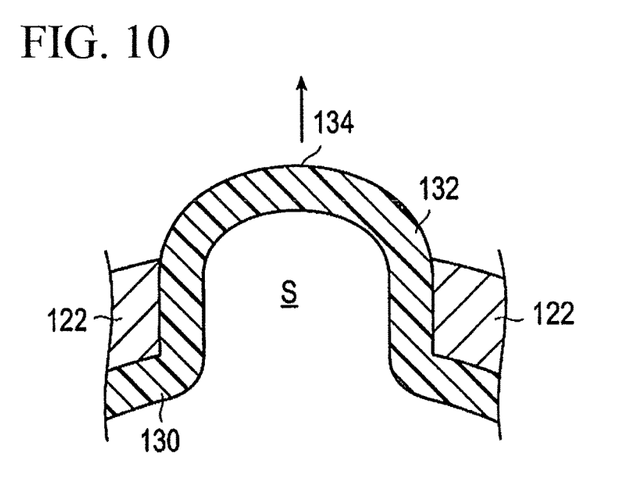
FIG. 10 is an enlarged view illustrating formation of the ridge portion of the balloon continuing from FIG. 9.

Set forth next with reference to FIGS. 8-10 is a description of a method for manufacturing the stent delivery system 100. The manufacturing method for the stent delivery system 100 includes a balloon fixing aspect, a stent attachment aspect, a ridge portion formation aspect and a concave portion formation aspect.

The balloon fixing aspect of the method involves first disposing the balloon 130 in the folded state in such a manner as to surround the outer periphery of the inner tube 162, and then fixing a proximal end portion of such balloon in a liquid-tight manner to the outer periphery of the distal end portion of the outer tube 164 positioned on the outer side of the inner tube 162 while also fixing a distal end portion of such balloon in a liquid-tight manner to the outer periphery of the distal end portion of the inner tube 162. Since the space between the inner peripheral surface of the outer tube 164 and the outer peripheral surface of the inner tube 162 constitutes the lumen 163 communicating with the injection port 142 of the hub 140, the inner side of the balloon 130 communicates with the injection port 142 of the hub 140. The fixing method is not limited to any specific manner, and examples include adhesive or heat bonding.

The stent attachment aspect involves disposing the stent 120 in a compressed state in which the diameter is reduced so that the stent surrounds the outer periphery of the balloon 130 as illustrated in FIG. 8. At this time, portions of the balloon 130 are not located in (sandwiched in) the spaces S between the struts 122 of the stent 120.

During the ridge portion formation aspect of the method, pressurized fluid supplied from the injection port 142 of the hub 140 is introduced into the balloon 130 through the lumen 163 of the shaft portion 160. The pressurized fluid applies pressure to the balloon 130 to inflate and outwardly expand the balloon 130 as shown in FIG. 9 so that part of the balloon 130 projects into the space S between the struts to sandwich the part of the balloon 130 between the struts 122, thereby forming the ridge portion 132 on the balloon 130 (refer to FIG. 10). It is to be noted that, when the ridge portion 132 is formed, it is also possible to raise the temperature of the stent 120 and the balloon 130.

Figure 11:
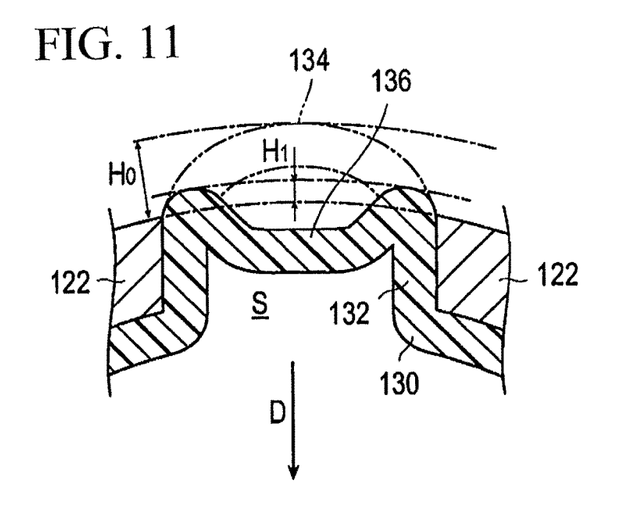
FIG. 11 an enlarged view illustrating formation of a concave portion at the ridge portion of the balloon continuing from FIG. 10.

The concave portion formation aspect of the method involves drawing out (sucking out) the fluid inside the balloon 130 by way of the injection port 142 of the hub 140 and the lumen 163 of the shaft portion 160. The pressure inside the balloon 130 is thus reduced. The reduction of the pressure of the balloon 130 recesses a top portion (central portion) 134 of the ridge portion 132 in the inward direction (in the direction toward the axis A of the shaft portion) D to form the concave portion 136 as shown in FIG. 11.

The projection amount H of the ridge portion 132 from the outer surface of the stent 120 varies from $H_0$, which is the projection amount before the formation of the concave portions 136, to $H_1$, which is the projection amount after the formation of the concave portion 136. In other words, since the projection amount H of the ridge portion 132 from the outer surface of the stent 120 decreases due to the presence of the concave portion 136, increase of the outer diameter is suppressed. Accordingly, it is possible to reduce the outer diameter of the distal portion of the stent delivery system 100. Further, since the side portion of each strut 122 of the stent 120 is engaged with the ridge portion 132 on the opposite sides of the concave portion 136 of the balloon 130, positional displacement and detachment (separation) of the stent from the balloon 130 are suppressed.

Because pressure in the balloon 130 is reduced after pressure is applied to the balloon 130 to inflate the balloon 130 to form the ridge portion 132, it is possible to relatively easily form the concave portion 136 at the top portion 134 of the ridge portion 132. Further, since the diameter of the stent 120 and the balloon 130 themselves decreases, reduction of the outer diameter of the distal portion can be achieved and the engagement strength between the stent 120 and the balloon 130 can be enhanced.

Figure 12:
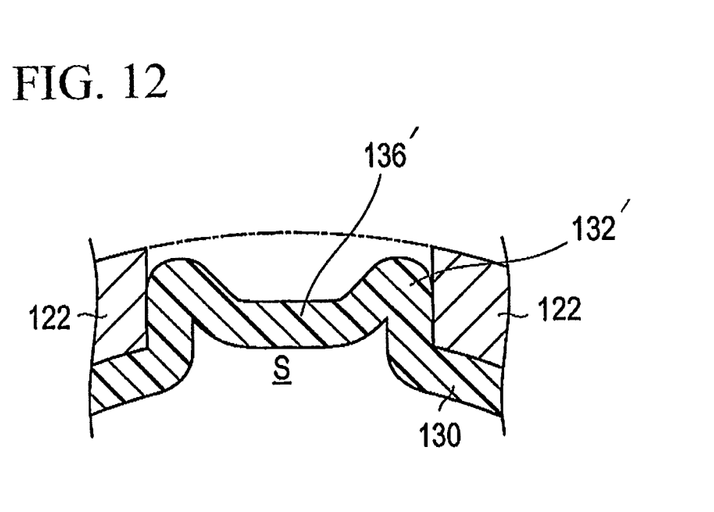
FIG. 12 is a cross-sectional view illustrating a modified example of the embodiment shown in FIGS. 1-11.

A modified example of the stent delivery system 100 will now be described with reference to FIG. 12. In this embodiment described as another example of the stent delivery system and manufacturing method disclosed here, the concave portion formation aspect of the method is carried out to position the ridge portion 132' of the balloon 130 in the inside of the space S between the struts 122 by forming the concave portion 136'. In this case, the concave portion formation aspect of the method is carried out so that the ridge portion 132' of the balloon 130 does not project radially outwardly beyond the outer surface of the struts 122 as shown in FIG. 12 and so an increase of the outer diameter of the distal portion of the stent delivery system 100 is further suppressed, thus allowing minimization of the outer diameter of the distal portion of the stent delivery system 100. In the example shown in FIG. 12, the outermost surface of the ridge portions 132' is positioned radially inwardly of the outermost surface of the struts 122.

As described above, the stent delivery system disclosed here by way of several examples is configured so that the top portion (central portion) of the ridge portion of the balloon with which the stent is engaged has the concave portion recessed in the inward direction (in the direction toward the axis of the inner tube). Therefore, positional displacement and detachment (separation) of the stent from the balloon are suppressed, and an increase of the outer diameter of the distal portion is inhibited. Further, with the manufacturing method for the stent delivery system, the concave portion recessed in the inward direction is formed at the top portion of the ridge portion of the balloon with which the stent is engaged. Therefore, positional displacement and detachment (separation) of the stent from the balloon are suppressed, and in addition, it is possible to avoid an increase of the outer diameter of the distal portion of the stent delivery system to be manufactured. The disclosure here thus provides a stent delivery system having the distal end portion possessing a relatively small outer diameter, and also provides a manufacturing method for manufacturing such stent delivery system.

The present invention is not limited to the embodiment and modified example described above, but can be modified in various ways. For example, it is also possible to dispose another marker on the proximal portion side of the shaft portion or to dispose the guide wire port midway of the outer tube.

Also it is possible to coat the distal portion side of the balloon and the shaft portion with hydrophilic polymer. In this case, a coefficient of friction when the distal portion of the stent delivery system is brought into contact with blood or physiological saline decreases, and the lubrication performance (sliding performance) is enhanced. Therefore, the insertion performance into a lumen in a living body is enhanced. Examples of the hydrophilic polymer include cellulose-based polymeric substance such as hydroxypropyl cellulose, polyethylene oxide-based polymeric substance such as polyethylene glycol, maleic anhydride-based polymeric substance such as maleic anhydride copolymer like methyl vinyl ether maleic anhydride copolymer, acrylamide-based polymeric substance such as dimethyl acrylamide-glycidyl methacrylate copolymer, or water-soluble nylon.

Further, during the forming of the concave portion recessed toward the axis of the shaft portion at the top portion of the ridge portion, in place of decreasing the pressure to the balloon, compressive force may be applied from the outside to the top portion of the ridge portion to recess the top portion of the ridge portion toward the axis of the shaft.

The detailed description above describes features and aspects of embodiments of a stent delivery system and method of manufacturing such stent delivery system. But the invention here is not limited to the precise embodiments and variations described above and illustrated in the drawing figures. Changes, modifications and equivalents can be implemented without departing from the spirit and scope of the invention as defined in the accompanying claims. It is expressly intended that all such changes, modifications and equivalents which fall within the scope of the claims are embraced by the claims.

What is claimed is:

1. A method of manufacturing a stent delivery system comprised of a hollow shaft portion possessing a longitudinal axis, an inflatable balloon disposed on an outer periphery of a distal end portion of the shaft portion, and a stent disposed on an outer periphery of the balloon and having a plurality of interconnected struts with spaced apart spaces bounded by several of the struts, the stent delivery system being configured to introduce the stent into a living body the method comprising:

inflating the balloon so that parts of the balloon project into the spaces bounded by several of the struts to form ridge portions in a plurality of the spaces each sandwiched by the struts so that the stent is engaged with the balloon;

forming a concave portion, at a top portion of the ridge portions, wherein the concave portion is bound by ridge portions engaged with the struts and that are upstanding relative to the concave portion, and wherein the concave portion is recessed toward the longitudinal axis of the shaft portion, and wherein the concave portion is arranged between the plurality of interconnected struts such that the concave portion has a surface perpendicular to an inward direction toward the longitudinal axis of the shaft portion that does not overlap a strut of the plurality of interconnected struts, and the inward direction is perpendicular to the longitudinal axis of the shaft portion; and wherein the inflating of the balloon comprises applying pressure to an interior of the balloon, and the forming of the concave portion at the top portion of the ridge portion comprises reducing the pressure in the interior of the balloon.

2. The method according to claim 1, wherein the forming of the concave portion at the top portion of the ridge portion comprises:
   forming the concave portion at the top portion of the ridge portion until an outermost surface of the ridge portion of the balloon is positioned radially inwardly of an outermost surface of the struts.

3. The method according to claim 1, wherein the forming of the concave portion at the top portion of the ridge portion comprises:
   forming the concave portion at the top portion of the ridge portion until an outermost surface of the concave portion is positioned radially inwardly of an outermost surface of the struts.

4. The method according to claim 1, wherein the forming of the concave portion at the top portion of the ridge portion comprises:
   forming the concave portion at the top portion of the ridge portion until an outermost surface of the concave portion is positioned radially inwardly of an outermost surface of the struts, and an outermost surface of parts of the ridge portion on either side of the concave portion are positioned radially outwardly of the outermost surface of the struts.

5. The method according to claim 1, wherein the hollow shaft portion includes an inner tube, the longitudinal axis extending parallel to the inner tube.

6. The method according to claim 5, wherein the inner tube is configured to communicate with a guide wire port, the method further comprising:
   inserting a guide wire into the guide wire port and through the inner tube to a distal end of the stent delivery system.

7. The method according to claim 1, wherein the inflating of the balloon further comprises:
   introducing a fluid into the interior of the balloon via an injection port of the stent delivery system.

8. The method according to claim 7, wherein the forming of the concave portion at the top portion of the ridge portion further comprises:
   removing the fluid from the interior of the balloon.

9. A method of manufacturing a stent delivery system comprised of a hollow shaft portion possessing a longitudinal axis, an inflatable balloon disposed on an outer periphery of a distal end portion of the shaft portion, and a stent disposed on an outer periphery of the balloon and having a plurality of interconnected struts with spaced apart spaces bounded by several of the struts, the stent delivery system being configured to introduce the stent into a living body the method comprising:
   inflating the balloon so that parts of the balloon project into the spaces bounded by several of the struts to form ridge portions in a plurality of the spaces each sandwiched by the struts so that the stent is engaged with the balloon;
   forming a concave portion, at a top portion of the ridge portions, wherein the concave portion is bound by ridge portions engaged with the struts and that are upstanding relative to the concave portion, and wherein the concave portion is recessed toward the longitudinal axis of the shaft portion, and wherein the concave portion is arranged between the plurality of interconnected struts such that a central portion of the concave portion is parallel to the longitudinal axis of the shaft portion and the central portion does not overlap a strut of the plurality of interconnected struts in an inward direction toward the longitudinal axis of the shaft portion; and
   wherein the inflating of the balloon comprises applying pressure to an interior of the balloon, and the forming of the concave portion at the top portion of the ridge portion comprises reducing the pressure in the interior of the balloon.

10. The method according to claim 9, wherein the forming of the concave portion at the top portion of the ridge portion comprises:
   forming the concave portion at the top portion of the ridge portion until an outermost surface of the ridge portion of the balloon is positioned radially inwardly of an outermost surface of the struts.

11. The method according to claim 9, wherein the forming of the concave portion at the top portion of the ridge portion comprises:
   forming the concave portion at the top portion of the ridge portion until an outermost surface of the concave portion is positioned radially inwardly of an outermost surface of the struts.

12. The method according to claim 9, wherein the forming of the concave portion at the top portion of the ridge portion comprises:
   forming the concave portion at the top portion of the ridge portion until an outermost surface of the concave portion is positioned radially inwardly of an outermost surface of the struts, and an outermost surface of parts of the ridge portion on either side of the concave portion are positioned radially outwardly of the outermost surface of the struts.

13. The method according to claim 9, wherein the hollow shaft portion includes an inner tube, the longitudinal axis extending parallel to the inner tube.

14. The method according to claim 13, wherein the inner tube is configured to communicate with a guide wire port, the method further comprising:
   inserting a guide wire into the guide wire port and through the inner tube to a distal end of the stent delivery system.

15. The method according to claim 9, wherein the inflating of the balloon further comprises:
   introducing a fluid into the interior of the balloon via an injection port of the stent delivery system.

16. The method according to claim 15, wherein the forming of the concave portion at the top portion of the ridge portion further comprises:
   removing the fluid from the interior of the balloon.

* * * * *